(12) United States Patent
Meridew et al.

(10) Patent No.: US 8,535,387 B2
(45) Date of Patent: Sep. 17, 2013

(54) PATIENT-SPECIFIC TOOLS AND IMPLANTS

(75) Inventors: Jason D. Meridew, Warsaw, IN (US);
John R. White, Winona Lake, IN (US);
Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 32 days.

(21) Appl. No.: 13/041,665

(22) Filed: Mar. 7, 2011

(65) Prior Publication Data

US 2011/0160867 A1    Jun. 30, 2011

(51) Int. Cl.
*A61F 2/36* (2006.01)

(52) U.S. Cl.
USPC ..................................... 623/23.35; 623/23.15

(58) Field of Classification Search
USPC ...... 623/23.15, 23.21, 23.22, 23.35; 606/102
See application file for complete search history.

(56) References Cited

U.S. PATENT DOCUMENTS

| | | |
|---|---|---|
| 1,480,285 A | 1/1924 | Moore |
| 2,181,746 A | 11/1939 | Siebrandt |
| 2,407,845 A | 9/1946 | Nemeyer |
| 2,618,913 A | 11/1952 | Plancon et al. |
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,475,549 A | 10/1984 | Oh |
| 4,506,393 A | 3/1985 | Murphy |
| 4,524,766 A | 6/1985 | Petersen |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,695,283 A | 9/1987 | Aldinger |
| 4,696,292 A | 9/1987 | Heiple |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

(Continued)

*Primary Examiner* — Bruce E Snow
(74) *Attorney, Agent, or Firm* — Harness, Dickey

(57) ABSTRACT

A method for preparing a femoral neck for receiving a neck implant includes obtaining image data of a proximal femoral bone and femoral neck of a patient by a medical imaging method and constructing a three-dimensional image model of the proximal femoral bone and neck of the patient using the image data. The method further includes identifying a three-dimensional cortical boundary surface at an interface between cortical and cancellous bone of the patient using the image model. A patient-specific broach having a three-dimensional cutting surface closely matching and complementary to the cortical boundary surface of the patient using the image model is designed and manufactured.

12 Claims, 6 Drawing Sheets

(56) References Cited

U.S. PATENT DOCUMENTS

| | | |
|---|---|---|
| 4,703,751 A | 11/1987 | Pohl |
| 4,704,686 A | 11/1987 | Aldinger |
| 4,721,104 A | 1/1988 | Kaufman et al. |
| 4,722,330 A | 2/1988 | Russell et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A * | 6/1990 | Walker et al. ............... 128/898 |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,246,444 A | 9/1993 | Schreiber |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,671,018 A | 9/1997 | Ohara et al. |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |

| | | | |
|---|---|---|---|
| 6,427,698 B1 | 8/2002 | Yoon | |
| 6,459,948 B1 | 10/2002 | Ateshian et al. | |
| 6,463,351 B1 | 10/2002 | Clynch | |
| 6,475,243 B1 | 11/2002 | Sheldon et al. | |
| 6,482,236 B2 | 11/2002 | Habecker | |
| 6,488,715 B1 | 12/2002 | Pope et al. | |
| 6,503,255 B1 | 1/2003 | Albrektsson et al. | |
| 6,510,334 B1 | 1/2003 | Schuster et al. | |
| 6,514,259 B2 | 2/2003 | Picard et al. | |
| 6,517,583 B1 | 2/2003 | Pope et al. | |
| 6,520,964 B2 | 2/2003 | Tallarida et al. | |
| 6,533,737 B1 | 3/2003 | Brosseau et al. | |
| 6,547,823 B2 | 4/2003 | Scarborough et al. | |
| 6,554,837 B1 | 4/2003 | Hauri et al. | |
| 6,556,008 B2 | 4/2003 | Thesen | |
| 6,558,391 B2 | 5/2003 | Axelson, Jr. et al. | |
| 6,558,428 B2 | 5/2003 | Park | |
| 6,564,085 B2 | 5/2003 | Meaney et al. | |
| 6,567,681 B1 | 5/2003 | Lindequist | |
| 6,575,980 B1 | 6/2003 | Robie et al. | |
| 6,575,982 B1 | 6/2003 | Bonutti | |
| 6,591,581 B2 | 7/2003 | Schmieding | |
| 6,605,293 B1 | 8/2003 | Giordano et al. | |
| 6,622,567 B1 | 9/2003 | Hamel et al. | |
| 6,629,999 B1 | 10/2003 | Serafin, Jr. | |
| 6,641,617 B1 | 11/2003 | Merrill et al. | |
| 6,682,566 B2 | 1/2004 | Draenert | |
| 6,696,073 B2 | 2/2004 | Boyce et al. | |
| 6,697,664 B2 | 2/2004 | Kienzle, III et al. | |
| 6,701,174 B1 | 3/2004 | Krause et al. | |
| 6,709,462 B2 | 3/2004 | Hanssen | |
| 6,711,431 B2 | 3/2004 | Sarin et al. | |
| 6,711,432 B1 | 3/2004 | Krause et al. | |
| 6,712,856 B1 | 3/2004 | Carignan et al. | |
| 6,716,249 B2 | 4/2004 | Hyde | |
| 6,725,077 B1 | 4/2004 | Balloni et al. | |
| 6,738,657 B1 | 5/2004 | Franklin et al. | |
| 6,740,092 B2 | 5/2004 | Lombardo et al. | |
| 6,749,638 B1 | 6/2004 | Saladino | |
| 6,750,653 B1 | 6/2004 | Zou et al. | |
| 6,772,026 B2 | 8/2004 | Bradbury et al. | |
| 6,780,190 B2 | 8/2004 | Maroney | |
| 6,786,930 B2 | 9/2004 | Biscup | |
| 6,799,066 B2 | 9/2004 | Steines et al. | |
| 6,823,871 B2 | 11/2004 | Schmieding | |
| 6,827,723 B2 | 12/2004 | Carson | |
| 6,887,247 B1 | 5/2005 | Couture et al. | |
| 6,905,514 B2 | 6/2005 | Carignan et al. | |
| 6,923,817 B2 | 8/2005 | Carson et al. | |
| 6,923,831 B2 | 8/2005 | Fell et al. | |
| 6,932,842 B1 | 8/2005 | Litschko et al. | |
| 6,942,475 B2 | 9/2005 | Ensign et al. | |
| 6,944,518 B2 | 9/2005 | Roose | |
| 6,945,976 B2 | 9/2005 | Ball et al. | |
| 6,953,480 B2 | 10/2005 | Mears et al. | |
| 6,960,216 B2 | 11/2005 | Kolb et al. | |
| 6,990,220 B2 | 1/2006 | Ellis et al. | |
| 7,029,479 B2 | 4/2006 | Tallarida et al. | |
| 7,042,222 B2 | 5/2006 | Zheng et al. | |
| 7,048,741 B2 | 5/2006 | Swanson | |
| 7,050,877 B2 | 5/2006 | Iseki et al. | |
| 7,060,074 B2 | 6/2006 | Rosa et al. | |
| 7,074,241 B2 | 7/2006 | McKinnon | |
| RE39,301 E | 9/2006 | Bertin | |
| 7,104,997 B2 | 9/2006 | Lionberger et al. | |
| 7,105,026 B2 | 9/2006 | Johnson et al. | |
| 7,115,131 B2 | 10/2006 | Engh et al. | |
| 7,141,053 B2 | 11/2006 | Rosa et al. | |
| 7,169,185 B2 | 1/2007 | Sidebotham | |
| 7,176,466 B2 | 2/2007 | Rousso et al. | |
| 7,184,814 B2 | 2/2007 | Lang et al. | |
| 7,198,628 B2 | 4/2007 | Ondrla et al. | |
| 7,218,232 B2 | 5/2007 | DiSilvestro et al. | |
| 7,239,908 B1 | 7/2007 | Alexander et al. | |
| 7,241,315 B2 | 7/2007 | Evans | |
| 7,255,702 B2 | 8/2007 | Serra et al. | |
| 7,258,701 B2 | 8/2007 | Aram et al. | |
| 7,275,218 B2 | 9/2007 | Petrella et al. | |
| 7,282,054 B2 | 10/2007 | Steffensmeier et al. | |
| 7,294,133 B2 | 11/2007 | Zink et al. | |
| 7,297,164 B2 | 11/2007 | Johnson et al. | |
| 7,309,339 B2 | 12/2007 | Cusick et al. | |
| 7,333,013 B2 | 2/2008 | Berger | |
| 7,335,231 B2 | 2/2008 | McLean | |
| 7,371,260 B2 | 5/2008 | Malinin | |
| 7,383,164 B2 | 6/2008 | Aram et al. | |
| 7,385,498 B2 | 6/2008 | Dobosz | |
| 7,388,972 B2 | 6/2008 | Kitson | |
| 7,392,076 B2 | 6/2008 | Moctezuma de La Barrera | |
| 7,427,200 B2 | 9/2008 | Noble et al. | |
| 7,427,272 B2 | 9/2008 | Richard et al. | |
| 7,468,075 B2 | 12/2008 | Lang et al. | |
| 7,474,223 B2 | 1/2009 | Nycz et al. | |
| 7,488,325 B2 | 2/2009 | Qian | |
| 7,494,510 B2 * | 2/2009 | Zweymuller | 623/23.35 |
| 7,517,365 B2 | 4/2009 | Carignan et al. | |
| 7,527,631 B2 | 5/2009 | Maroney et al. | |
| 7,534,263 B2 | 5/2009 | Burdulis, Jr. et al. | |
| 7,542,791 B2 | 6/2009 | Mire et al. | |
| 7,559,931 B2 | 7/2009 | Stone | |
| 7,575,602 B2 | 8/2009 | Amirouche et al. | |
| 7,578,851 B2 | 8/2009 | Dong et al. | |
| 7,582,091 B2 | 9/2009 | Duncan et al. | |
| 7,591,821 B2 | 9/2009 | Kelman | |
| 7,601,155 B2 | 10/2009 | Petersen | |
| 7,604,639 B2 | 10/2009 | Swanson | |
| 7,611,516 B2 | 11/2009 | Maroney | |
| 7,618,451 B2 | 11/2009 | Berez et al. | |
| 7,621,915 B2 | 11/2009 | Frederick et al. | |
| 7,625,409 B2 | 12/2009 | Saltzman et al. | |
| 7,646,161 B2 | 1/2010 | Albu-Schaffer et al. | |
| 7,651,501 B2 | 1/2010 | Penenberg et al. | |
| 7,670,345 B2 | 3/2010 | Plassky et al. | |
| 7,682,398 B2 | 3/2010 | Croxton et al. | |
| 7,695,477 B2 | 4/2010 | Creger et al. | |
| 7,695,521 B2 | 4/2010 | Ely et al. | |
| 7,699,847 B2 | 4/2010 | Sheldon et al. | |
| 7,704,253 B2 | 4/2010 | Bastian et al. | |
| 7,723,395 B2 | 5/2010 | Ringeisen et al. | |
| 7,780,672 B2 | 8/2010 | Metzger et al. | |
| 7,780,740 B2 | 8/2010 | Steinberg | |
| 7,794,466 B2 | 9/2010 | Merchant et al. | |
| 7,794,467 B2 | 9/2010 | McGinley et al. | |
| 7,794,504 B2 | 9/2010 | Case | |
| 7,806,896 B1 | 10/2010 | Bonutti | |
| 7,809,184 B2 | 10/2010 | Neubauer et al. | |
| 7,819,925 B2 | 10/2010 | King et al. | |
| 7,828,806 B2 | 11/2010 | Graf et al. | |
| 7,879,109 B2 | 2/2011 | Borden et al. | |
| 7,892,261 B2 | 2/2011 | Bonutti | |
| 7,896,921 B2 | 3/2011 | Smith et al. | |
| 7,935,119 B2 | 5/2011 | Ammann et al. | |
| 7,935,150 B2 | 5/2011 | Carignan et al. | |
| 7,938,861 B2 | 5/2011 | King et al. | |
| 7,959,637 B2 | 6/2011 | Fox et al. | |
| 7,962,196 B2 | 6/2011 | Tuma | |
| 7,963,968 B2 | 6/2011 | Dees, Jr. | |
| 7,967,823 B2 | 6/2011 | Ammann et al. | |
| 7,967,868 B2 | 6/2011 | White et al. | |
| 7,974,677 B2 | 7/2011 | Mire et al. | |
| 7,981,158 B2 | 7/2011 | Fitz et al. | |
| 7,993,353 B2 | 8/2011 | Rossner et al. | |
| 8,062,301 B2 | 11/2011 | Ammann et al. | |
| 8,070,752 B2 | 12/2011 | Metzger et al. | |
| 8,083,745 B2 | 12/2011 | Lang et al. | |
| 8,083,746 B2 | 12/2011 | Novak | |
| 8,083,749 B2 | 12/2011 | Taber | |
| 8,086,336 B2 | 12/2011 | Christensen | |
| 8,092,465 B2 | 1/2012 | Metzger et al. | |
| 8,133,230 B2 | 3/2012 | Stevens et al. | |
| 8,133,234 B2 | 3/2012 | Meridew et al. | |
| 8,137,406 B2 | 3/2012 | Novak et al. | |
| 8,167,951 B2 | 5/2012 | Ammann et al. | |
| 8,170,641 B2 | 5/2012 | Belcher | |
| 8,182,489 B2 | 5/2012 | Horacek | |
| 8,192,441 B2 | 6/2012 | Collazo | |
| 8,211,112 B2 | 7/2012 | Novak et al. | |
| 8,241,292 B2 | 8/2012 | Collazo | |

| | | |
|---|---|---|
| 8,241,293 B2 | 8/2012 | Stone et al. |
| 8,265,790 B2 | 9/2012 | Amiot et al. |
| 8,282,646 B2 | 10/2012 | Schoenefeld et al. |
| 8,298,237 B2 | 10/2012 | Schoenefeld et al. |
| 8,303,596 B2 | 11/2012 | Pla.beta.ky et al. |
| 8,333,772 B2 | 12/2012 | Fox et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |

| Pub. No. | Date | Inventor |
|---|---|---|
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0254093 A1 | 10/2009 | White et al. |

| | | |
|---|---|---|
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0022049 A1 | 1/2011 | Huebner et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0065640 A1 | 3/2012 | Metzger et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0209276 A1 | 8/2012 | Schuster |
| 2012/0215225 A1 | 8/2012 | Philippon et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0265208 A1 | 10/2012 | Smith |
| 2012/0271314 A1 | 10/2012 | Stemniski et al. |
| 2012/0271366 A1 | 10/2012 | Katrana et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2013/0001121 A1 | 1/2013 | Metzger |
| 2013/0006250 A1 | 1/2013 | Metzger et al. |
| 2013/0035766 A1 | 2/2013 | Meridew |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |

| | | |
|---|---|---|
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096557 A2 | 8/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

Great Britain Search Report mailed Dec. 21, 2011 for GB1116054.6, claiming benefit of U.S. Appl. No. 12/888,005, filed Sep. 22, 2010.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

Thoma, W., et al., "Endoprothetischen Versorgung des Kniegelenks auf der Basis eines 3D-computertomographischen Subtraktionsverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (Oct. 31, 1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (Dec. 31, 2008) pp. 1-25.

"Discovery® Elbow System," brochure. Biomet Orthopedics, Inc. (Nov. 30, 2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (Mar. 31, 2004) pp. 1-8 (12 sheets).

"Patient Matched PMI Implants, C.A.M.R.A. 3-D Imaging," brochure, Biomet, Inc. (Jan. 31, 1991) 6 pages.

"Regenerex® Tibial Cone Augment, Surgical Technique Addendum to the Vanguard® SSK Revision System," brochure. Biomet® Orthopedics. (Mar. 31, 2010) pp. 1-8 (12 sheets).

"Signature™ Personalized Patient Care, Surgical Technique Addendum to the Vanguard Knee System" brochure. Biomet® Orthopedics, Inc. (May 15, 2009) pp. 1-8.

"TruMatch™ Personalized knee replacement solutions,"tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics (Aug. 31, 2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Charl P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (Sep. 13, 2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazan, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Dec. 22, 2011 for PCT/US2010/038177 claiming benefit of U.S. Appl. No. 12/483,807, filed Jun. 12, 2009.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability for PCT/US2010/050701 mailed Apr. 12, 2012 claiming benefit of U.S. Appl. No. 12/571,969, filed Oct. 1, 2009.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756057, filed May 31, 2007.

International Search Report and Written Opinion for PCT/US2009/039507 mailed Jul. 14, 2009, claiming benefit of U.S. Appl. No. 12/103,824, filed Apr. 16, 2008.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Aug. 24, 2010 for PCT/US2010/038177 claiming benefit of U.S. Appl. No. 12/483,807, filed Jun. 12, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

International Search Report mailed Nov. 30, 2010 for PCT/EP2010/061630 filed Aug. 10, 2010 claiming benefit of DE102009028503.2 filed Aug. 13, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc, (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research 354, pp. 28-38 (Sep. 1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (May 2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (Jul. 2006).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Biomet "Oxford® Partial Knee" brochure, 8 pages (Feb. 2011).

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

"Comprehensive® Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

Friedman, R.J. et al., "The Use Of Computerized Tomography In The Measurement Of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478 filed Aug. 29, 2011.

International Search Report and Written Opinion mailed Feb. 6, 2013 for PCT/US2012/060842, which claims benefit of U.S. Appl. No. 13/653,868, filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

* cited by examiner

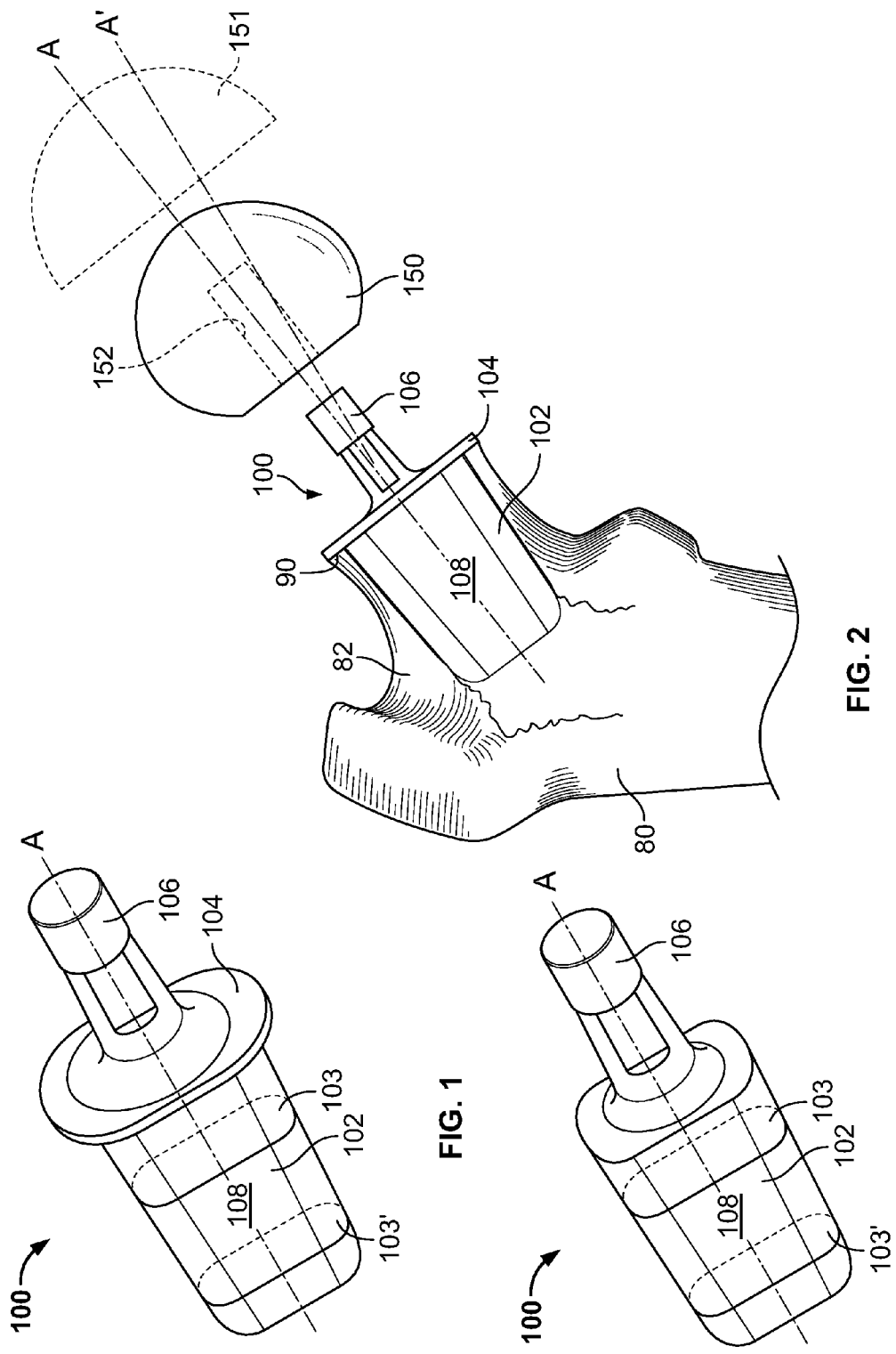

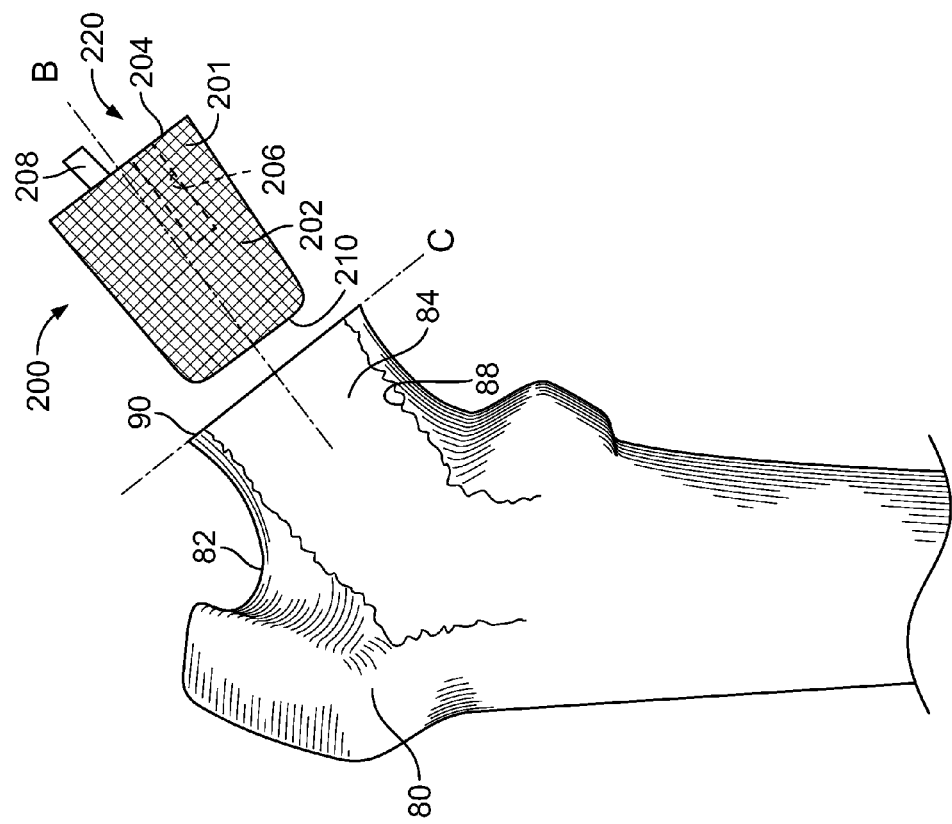
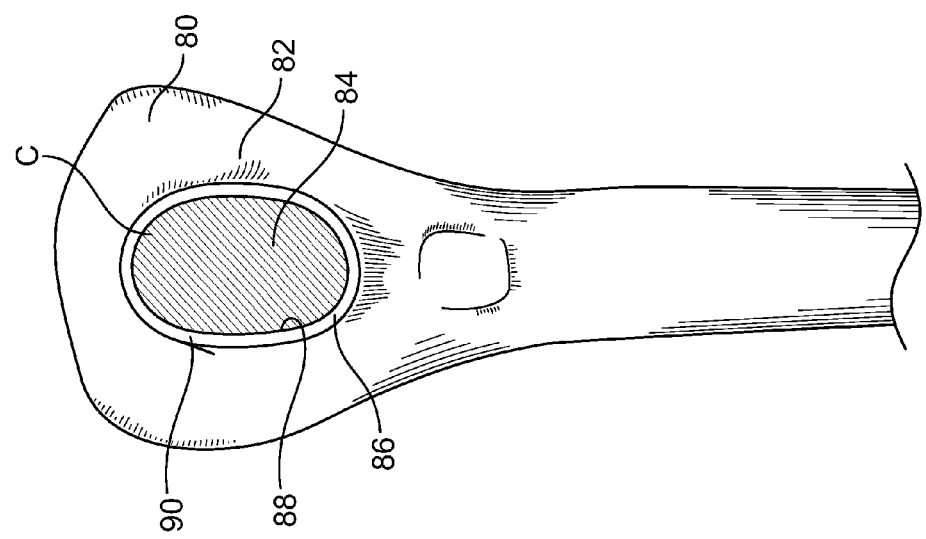
FIG. 4
FIG. 3

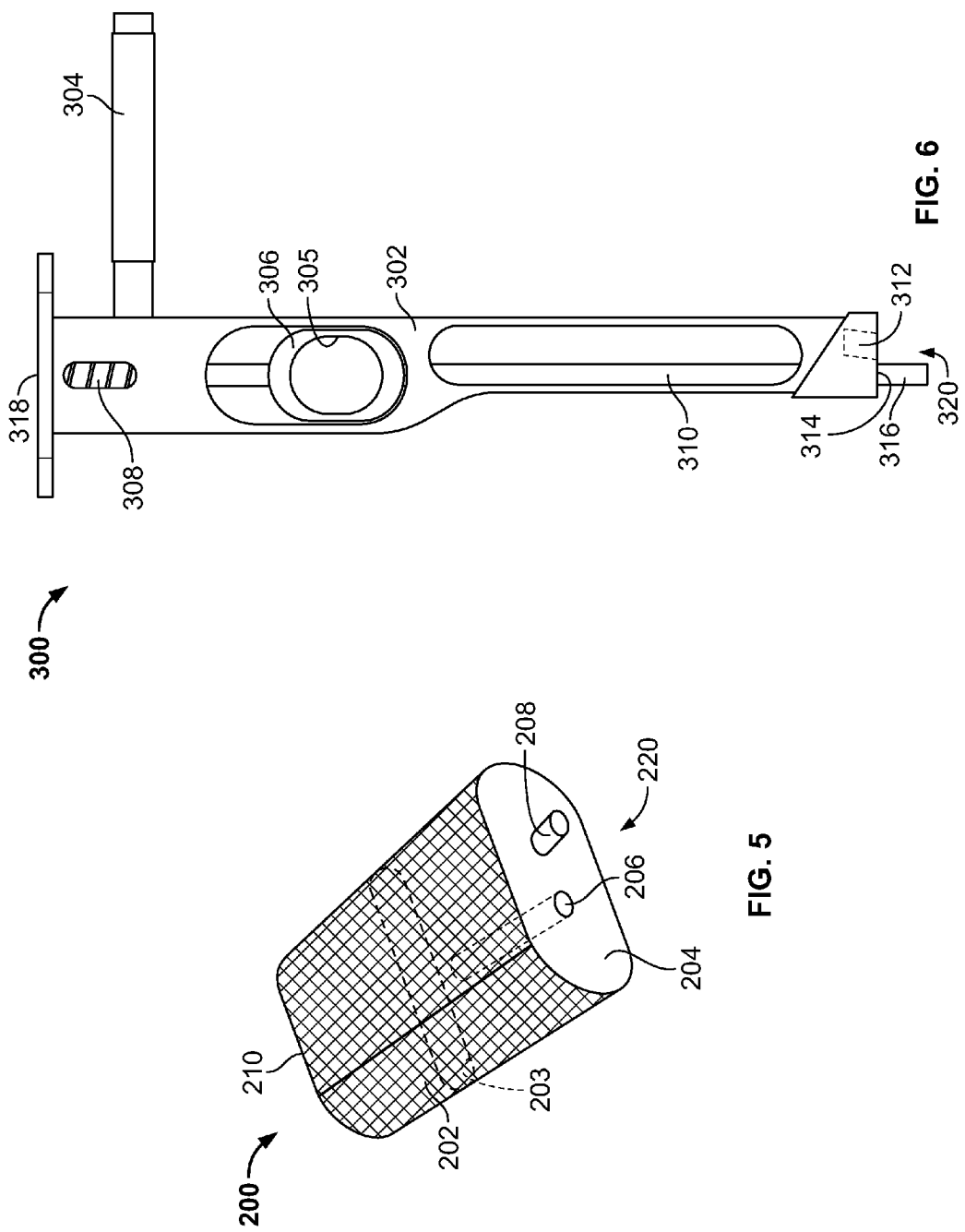

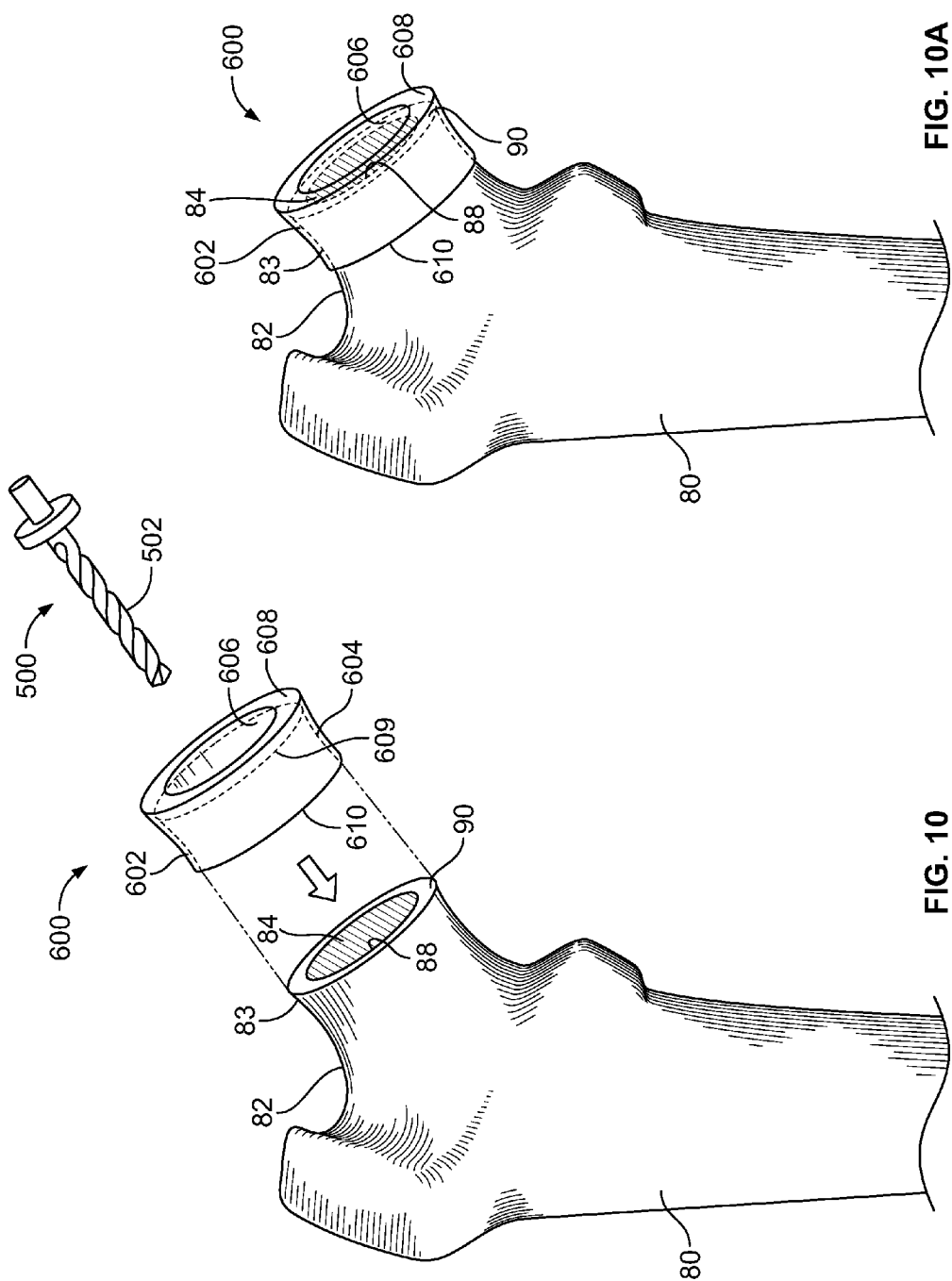

PATIENT-SPECIFIC TOOLS AND IMPLANTS

INTRODUCTION

The present teachings provide a bone-preserving design for a hip prosthesis. More specifically, the present teachings are directed to patient-specific femoral neck implants and associated tools and methods

SUMMARY

The present teachings provide various methods, tools and implants for preparing a femoral neck to receive a neck implant.

The present teachings provide a method for preparing a femoral neck for receiving a neck implant. The method includes obtaining image data of a proximal femoral bone and femoral neck of a patient by a medical imaging method and constructing a three-dimensional image model of the proximal femoral bone and neck of the patient using the image data. The method further includes identifying a three-dimensional cortical boundary surface at an interface between cortical and cancellous bone of the patient using the image model. A patient-specific broach having a three-dimensional cutting surface closely matching and complementary to the cortical boundary surface of the patient using the image model is designed and manufactured.

Another method according to the present teachings includes resecting a femoral head from a femoral neck of a patient according to a pre-operative patient-specific plan. The method further includes removing only cancellous bone from the femoral neck and proximal femoral bone of the patient using a patient-specific broach having a three-dimensional cutting surface closely matching and complementary to a cortical/cancellous bone interface surface of the femoral neck of the patient.

The present teachings provide a femoral neck implant. The femoral neck implant includes a body for implantation into a femoral neck of a patient. The body has a patient-specific cross-section of variable size and shape along a longitudinal axis of the body and a patient-specific three-dimensional outer surface that closely nests and conforms complementarily to a cortical boundary surface corresponding to a cortical/cancellous bone interface surface of the femoral neck of the specific patient after removing only the cancellous bone from the femoral neck. The neck implant can include a neck portion extending from the body and configured for coupling with a femoral head implant.

The present teachings provide a femoral neck cutting tool, such as a broach for preparing a femoral neck for a femoral neck implant. The cutting tool includes a body having a patient-specific cross-section of variable size and shape along a longitudinal axis and a patient-specific three-dimensional outer cutting surface that closely nests and conforms complementarily to a cortical boundary surface corresponding to a cortical/cancellous bone interface surface of a femoral neck of the specific patient and configured for removing only the cancellous bone from the femoral neck of the patient. The cutting tool can include a non patient-specific coupling component for engaging a non patent-specific driver tool.

The present teachings also provide a patient-specific guide for preparing a femoral neck of a patient for receiving a femoral neck implant. The patient-specific guide includes a first wall having a first inner surface with a patient-specific inner bore therethrough, and a peripheral wall extending from the first wall. The first inner surface is configured to mate with a resected surface of the femoral neck. The peripheral wall includes a three-dimensional patient-specific peripheral inner surface configured to mate in only one position with an outer peripheral surface of the femoral neck after resection.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1 is a perspective view of a patient-specific neck implant according to the present teachings;

FIG. 1A is a perspective view of a patient-specific neck implant according to the present teachings;

FIG. 2 is an environmental view of the neck implant of FIG. 1;

FIG. 3 is a plan view of the proximal femur showing a resection of the femoral neck at a plane C;

FIG. 4 is an environmental view showing a patient-specific broach for the femoral neck implant;

FIG. 5 is a perspective view of a patient-specific broach according to the present teachings;

FIG. 6 is a plan view of a driver tool for the broach of FIG. 5;

FIG. 10 is an exploded environmental view of a patient-specific cutting guide for a neck implant according to the present teachings; and FIG. 10A is an environmental view of the cutting guide of FIG. 10.

DESCRIPTION OF VARIOUS EMBODIMENTS

Figure 7:
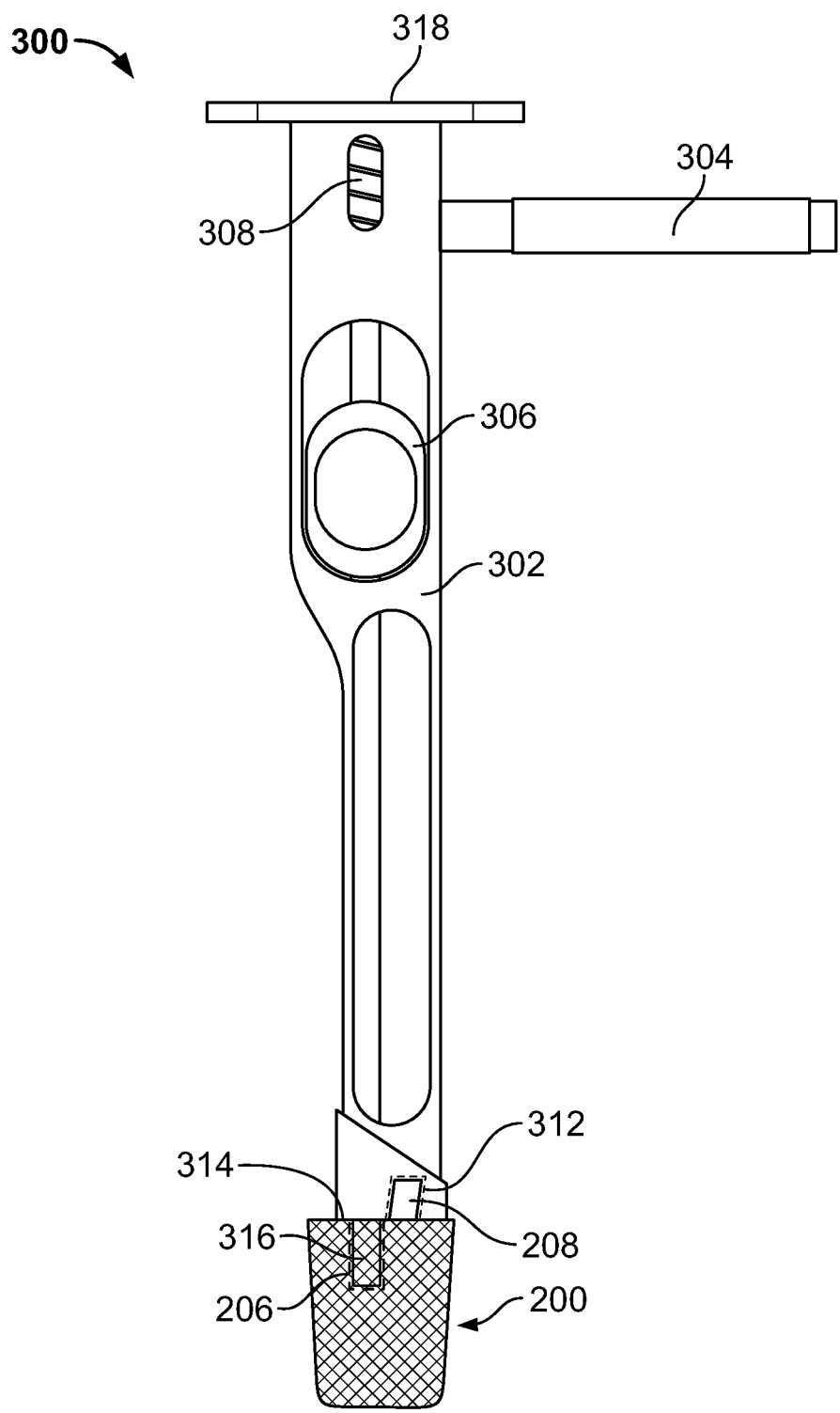
FIG. 7 is a plan view of the driver tool of FIG. 6 coupled to the broach of FIG. 5.

The following description is merely exemplary in nature and is in no way intended to limit the present teachings, applications, or uses.

The present teachings provide patient-specific tools and implants designed for a conservative hip procedure that conserves a portion of femoral neck of a specific patient.

As described in commonly assigned U.S. application Ser. No. 11/756,057, filed on May 31, 2007, during a preoperative planning, imaging data of the relevant anatomy of a patient can be obtained at a medical facility or doctor's office. The imaging data can include, for example, a detailed scan of a pelvis, hip, knee, ankle or other joint or relevant portion of the patient's anatomy. The imaging data can be obtained using MRI, CT, X-Ray, ultrasound or any other imaging system. The imaging data obtained can be used to construct a three-dimensional computer image of the joint and prepare an initial pre-operative plan that can include bone or joint preparation, including planning for resections, milling, reaming, broaching, implant selection and fitting, design of patient-specific guides, templates, tools and alignment protocol for the surgical procedure.

Computer modeling for obtaining three-dimensional computer images of the relevant patient's anatomy can be provided by various CAD programs and/or software available from various vendors or developers, such as, for example, from Materialise USA, Plymouth, Mich. The computer modeling program can be used to plan a preoperative surgical plan, including planning various bone preparation procedures, selecting or designing/modifying implants and designing patient-specific guides and tools including patient-specific prosthesis components, and patient-specific tools, including reaming, broaching, milling, drilling or cutting tools, alignment guides, templates and other patient-specific instruments.

The pre-operative plan can be stored in any computer storage medium, in a computer file form or any other computer or digital representation. The pre-operative plan, in a digital form associated with interactive software, can be made available via a hard medium, a web-based or mobile or cloud service, a cellular portable device to the surgeon or other medical practitioner, for review. Using the interactive software, the surgeon can review the plan, and manipulate the position of images of various implant components relative to an image of the anatomy. The surgeon can modify the plan and send it to the manufacturer with recommendations or changes. The interactive review process can be repeated until a final, approved plan, is sent to the manufacturer.

After the surgical plan is approved by the surgeon, patient-specific implants and associated tools, including, for example, alignment guides, cutting/milling/reaming/broaching or other tools for the surgical preparation of the joint or other anatomy portion of the specific patient can be designed using a CAD program or other three-dimensional modeling software, such as the software provided by Materialise, for example, according to the surgical plan. Computer instructions of tool paths for machining the patient-specific tools and/or implants can be generated and stored in a tool path data file. The tool path data can be provided as input to a CNC mill or other automated machining system, and the tools and implants can be machined from polymer, ceramic, metal or other suitable material depending on the use, and sterilized. The sterilized tools and implants can be shipped to the surgeon or medical facility for use during the surgical procedure.

Patient-specific components or tools or portions discussed below are generally constructed by a surgical plan approved by the surgeon using three-dimensional images of the specific patient's anatomy and made to closely conform and mate substantially as a negative mold of corresponding portions of the patient's anatomy, including bone surfaces with or without associated soft tissue. MRI scans, for example, allow modeling of soft tissue, such as articular cartilage, and modeling of bone portions of different densities, such as inner surfaces matching cortical and cancellous bone, as discussed below.

The present teachings provide a bone-preserving design for a hip prosthesis and associated tools. The procedure can conserve as much of the natural femoral neck 82 of the patient as determined by the surgeon depending on the specific patient by providing a patient-specific femoral neck implant 100 for supporting a femoral head implant 150, as illustrated in FIGS. 1, 1A and 2.

Referring to FIGS. 1 and 1A, an exemplary patient-specific neck-preserving ("neck implant" for short) 100 can include a body or stem 102 for introduction into the femoral neck 82 as described below and an optional flange or collar 104 for abutment on a resected surface 90 corresponding to a resection plane C of the femoral neck 82 (shown in FIG. 4). A neck implant 100 without the collar 104 is illustrated in FIG. 1A. The neck implant 100 can also include a neck portion 106 which can be coupled to a corresponding bore 152 of the femoral head implant 150 using a taper-to-taper connection or other type of coupling. The stem 102 of the neck implant 100 is designed to be patient-specific with a three-dimensional outer surface 108 that is complementary and closely nests and conforms to a cortical/cancellous interface surface 88 where the cortical and cancellous bone layers meet (referred to as cortical boundary surface 88 after the cancellous bone is removed) of the femoral neck 82 of the patient only in one position. Identifying the cortical/cancellous interface 88 enables removing only the cancellous bone 84, thereby conserving the hard cortical bone unmodified for engaging the complementary outer surface 108 of the neck implant 100.

Specifically, the neck implant 100 is designed during the pre-operative plan based on a three-dimensional computer model of the femoral neck 82 of the patient as reconstructed from MRI, CT, X-ray or other scans of the patient. Referring to FIG. 3, the cortical/cancellous interface surface 88 between the cortical bone 86 and the cancellous bone 84 is illustrated after a planar neck resection C is made to separate the natural femoral head from the portion of the femoral neck 82 to be preserved below resected surface 90. As can be seen from FIG. 2, the neck implant 100 can be sized and shaped such that it does not extend beyond the femoral neck 82 into the intramedullary canal of the femoral bone of the patient. The neck implant 100 has a patient-specific depth into the femoral neck 82 and a patient-specific angle relative to the femur. Further, because the cortical/cancellous interface surface 88 has a variable size and shape cross-section, the neck implant 100 has a corresponding variable size and shape cross-section along a longitudinal axis A of the neck implant 100, which is also specific to each patient. For simplicity, the neck implant 100 is shown in FIG. 1 with a variable oval/elongated and tapering cross-section 103, 103' (in two different locations), although it should be understood that this geometry is merely exemplary and that the shape and size cross-section 103 along the body of the neck implant 100 is patient-specific and mirrors the corresponding shape and size of the cortical/cancellous interface surface 88 along the femoral neck 82 of the specific patient. The cross-section 103 can be oval or elongated and decreasing or tapering in size, but not necessarily linearly. Further, the cross-section 103 may be and generally is non-symmetric for a specific patient. The neck portion 106 of the neck implant 100 can also be designed to be aligned to a patient-specific articulation direction along a second axis A' which may be at an angle to the longitudinal axis A of the neck implant A, as illustrated in FIG. 2. The neck portion 106 can be also adjusted for an out-of-plane angle or neck version adjustment.

Referring to FIGS. 3-5, to remove only the spongy cancellous bone 84 while preserving substantially all the cortical bone 86, a patient-specific cutting tool, broach or other bone-removing tool 200 can be designed during the preoperative plan based on the three-dimensional computer model of the neck 82 of the patient. Specifically, the broach 200 is designed to have a body 201 with an outer peripheral three-dimensional cutting surface 202 extending from a proximal end surface 204 to a distal end surface 210 of the body 201 that closely nests and conforms or matches and is complementary to the cortical/cancellous interface surface 88 only in one position and such that only cancellous bone 84 is removed and the cortical boundary surface 88 is exposed and maintained. Similarly to the neck implant 100, the broach 200 is also a patient-specific and has a variable in shape and size cross-section 203, which is generally oval/elongated and tapering, but not necessarily linearly, along a longitudinal axis B of the broach. Further, the cross-section 203 may be non-symmetric for a specific patient. The cutting surface 202 is provided with cutting teeth and channels or grooves for moving bone chips away from the cavity created by the broach 200, as shown in FIG. 4.

Referring to FIGS. 5-7, the patient-specific broach 200 can be coupled to a non-custom driver tool 300 by providing a coupling interface between the proximal end surface 204 of the broach to a distal surface 314 of the driver tool 300. The coupling interface can include, for example, a broach coupling component 220, such as a finger or rod or other protrusion 208 extending from the proximal end surface 204 of the broach 200 to be received in a corresponding bore or other opening 312 defined through the distal surface 314 of the driver tool 300. The coupling interface can also include a driver coupling component 320, such as an opening or bore 206 defined through the proximal end surface 204 for receiving a distal portion 316 of a retractable bar or rod 310 of the driver tool 300. The driver tool 300 can include a body 302, a handle bar 304, and a proximal flange 318 for impaction. The retractable rod 310 extends along the length of the body 302 and is biased by a proximal spring 308. The rod 310 can be deployed for engaging the broach 200 by using a trigger 306 which can be operated by holding with one hand the handle 304 and squeezing the trigger opening 305 with an index finger. The broach 200 can be held securely with the driver tool 300, as shown in FIG. 7 and inserted into the femoral neck 82 to remove the cancellous bone 84 and expose the cortical/cancellous interface surface 88 for receiving the patient-specific neck implant, as shown in FIGS. 1 and 2.

Figure 8:
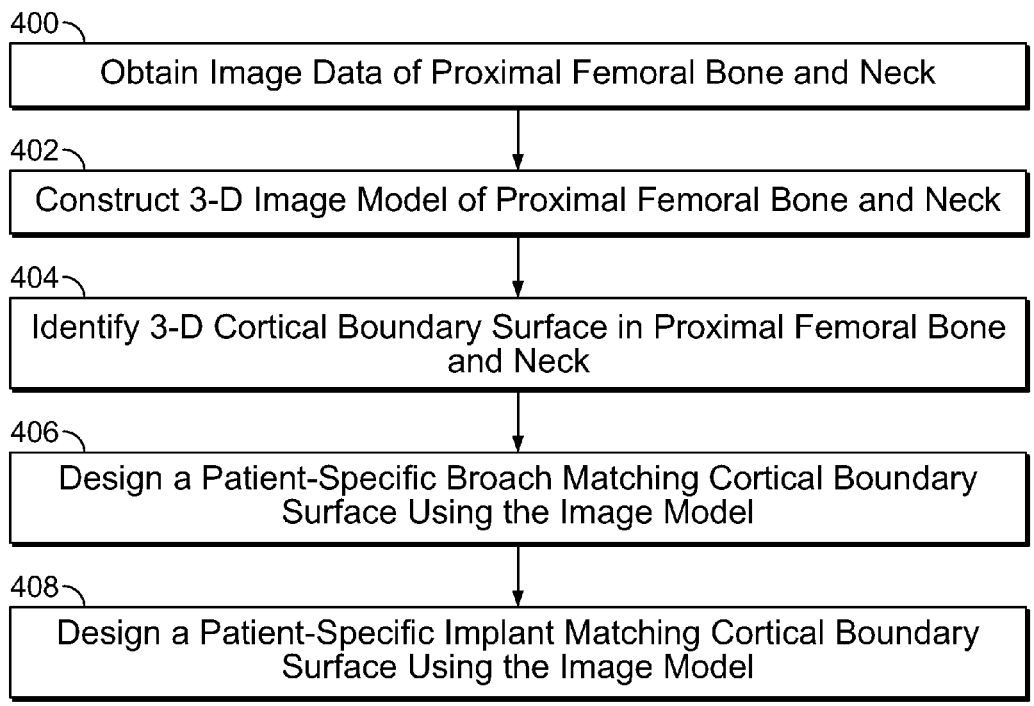
FIG. 8 is a flow chart of a method according to the present teachings.
Figure 9:
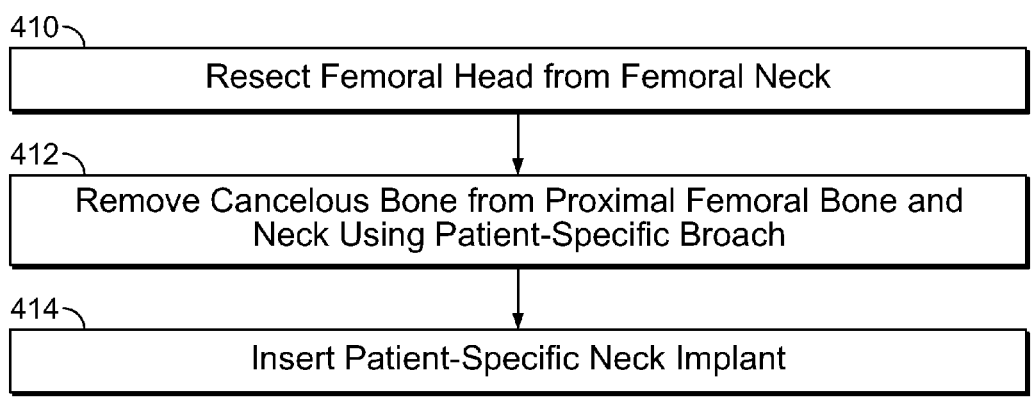
FIG. 9 is a flow chart of a method according to the present teachings.

Referring to FIGS. 8 and 9 according to present teachings, image data from CT, MRI, X-ray, ultrasound or other scanning of the proximal femoral bone 80 and femoral neck 82 of a patient are obtained at block 400. For modeling the cortical/cancellous interface and identifying the cortical boundary surface 88, the image data may be obtained from MRI scanning or other methods that provide differentiation of bone and tissue layers based on density, composition or other parameters. A three-dimensional computer image model of the proximal femoral bone 80 and femoral neck 82 of the patient can be constructed at block 402 using commercially available software, as discussed above. The three-dimensional cortical boundary surface 88 can be visible and identified and confirmed in the image model at block 404 by the surgeon. A neck resection plane can be selected and corresponding patient-specific femoral alignment guides and/or femoral head resection guides can be designed, as discussed, for example, in commonly assigned U.S. application Ser. No. 12/893,306, filed Sep. 29, 2010 and U.S. application Ser. No. 12/486,992, filed Jun. 18, 2009 of the cross-reference section, and incorporated herein by reference. A patient-specific broach 200 having a three-dimensional cutting surface 202 matching and complementary to the cortical boundary surface 88 in only one position can be designed at block 406 using the computer image model of the patient's anatomy. A patient-specific neck implant 100 having a three-dimensional surface 108 matching and complementary to the cortical boundary surface 88 in only one position can be designed and manufactured using the computer image model of the patient's anatomy (block 408). The implant 100 can be impacted into the femoral neck 82 and can also be porous coated for bone in-growth. As discussed above, other patient-specific tools, including femoral alignment/cutting guides to be used for resecting the femoral head, can also be designed and manufactured using the image model of the patient's anatomy according to the pre-operative plan.

The patient-specific neck implant 100, patient-specific broach 200 and other custom or non-custom tools are sterilized and shipped to the surgeon's site. Referring to FIG. 9, intra-operatively, the natural femoral head can be resected from the femoral neck 82 at a selected position and orientation (plane C in FIG. 4) using, for example, patient-specific alignment guides, patient-specific resection guides, non-custom guides and cutting tools or combinations thereof (block 410). The resection plane C is selected to preserve as much of the natural femoral neck 82 as determined in the pre-operative plan. After the natural femoral head is removed intra-operatively, the patient-specific broach 200 can be used to remove only the cancellous bone 84 from the femoral neck 82 and expose the cortical boundary surface 88 of the femoral neck 82, at block 412. The patient-specific neck implant 100 can then be implanted, for example, by impaction, in only one position (block 414), and mate with the exposed cortical boundary surface 88, as shown in FIG. 2. A femoral head implant 150 can be coupled to the neck portion 106 of the neck implant 100. The femoral head implant 150 can articulate with the natural acetabulum or an acetabular implant 151, as determined and planned by the surgeon for the specific patient.

Referring to FIGS. 10 and 10A, in some embodiments, a patient-specific milling or cutting guide 600 can be used with a milling tool 500 to remove the cancellous bone 84 and prepare the femoral neck 82 for receiving a neck implant 100. The patient-specific milling guide 600 can be designed during the preoperative plan such that it can be mounted only in one position on the femoral neck 82, after the femoral head is resected and removed. The milling guide 600 can include a peripheral wall 602 and a first wall 608. The first wall 608 can be substantially flat and have a first inner surface 609. The peripheral wall 602 extends from the first wall 608 to a second surface 610 that is opposite the first wall 608. The peripheral wall 602 includes a three-dimensional patient-specific peripheral inner surface 604 that is configured to nestingly mate and conform only in one position to a remaining (after resection) three-dimensional outer peripheral surface 83 of the femoral neck 82. The first wall 608 includes a patient-specific bore 606 therethrough. The first inner surface 609 is patient-specific and configured to mate and conform to the resected surface 90, as shown in FIGS. 10 and 10A. The patient-specific bore 606 is sized and shaped during the pre-operative plan to be patient-specific for guiding a cutting portion 502 of a milling or other cutting tool 500 to remove the cancellous bone 84 from the femoral neck 82 to the cortical boundary 88 (interface between cortical and cancellous bone) for receiving a neck implant, such as the patient-specific neck implant 100 discussed above. It is noted that the dimensions the patient-specific milling guide 600, including the depth and size the peripheral inner surface 604, is such that the patient-specific milling guide 600 can be mounted over the resected femoral neck 82. In some embodiments, the patient-specific milling guide can include a split or hinge (not shown) along the insertion axis or can be formed in two pieces couplable pieces in clamshell fashion, as discussed in commonly assigned U.S. patent application Ser. No. 12/486,992, filed Jun. 18, 2009 and incorporated herein by reference.

The patient-specific broach 200, the patient-specific milling guide 600 and the patient-specific implant 100 can be manufactured from biocompatible materials using machining, rapid manufacturing by stereolithography, laser welding, computer-assisted manufacturing using numerical machining or robotic controllers. Patient-specific alignment and/or resection guides for resecting and removing the femoral head can also be designed from the image model and manufactured by the above methods according to the pre-operative plan for the patient.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for preparing a femoral neck for receiving a neck implant comprising:
    obtaining image data of a proximal femoral bone and femoral neck of a specific patient by a medical imaging method;
    constructing a three-dimensional image model of the proximal femoral bone and neck of the specific patient using the image data;
    identifying a three-dimensional cortical boundary surface at an interface between cortical and cancellous bone of the specific patient using the three-dimensional image model;
    designing a patient-specific broach having a three-dimensional cutting surface matching as a negative mold the cortical boundary surface of the specific patient using the three-dimensional image model and configured for removing the cancellous bone without removing the cortical bone;
    manufacturing the patient-specific broach;
    designing a patient-specific neck implant having a body with a three-dimensional outer surface matching as a negative mold of the cortical boundary surface of the patient using the three-dimensional image model;
    manufacturing the patient-specific neck implant; and
    sizing the neck implant to extend only into the femoral neck of the specific patient and have a patient-specific length determined from the three-dimensional image model of the specific patient.

2. The method of claim 1, wherein the image data includes data obtained from any of MRI, CT, X-ray, ultrasound imaging methods.

3. The method of claim 1, wherein the neck implant includes a planar flange coupled to the body, the flange configured for engaging a resected surface of the femoral neck of the patient.

4. The method of claim 3, wherein the neck implant includes a neck portion extending from the body for coupling to a femoral head component at a patient-specific articulation axis having an orientation determined from the three-dimensional image model of the specific patient.

5. The method of claim 1, wherein obtaining image data of a proximal femoral bone and femoral neck of a specific patient includes obtaining the image data using at least one of MRI and ultrasound imaging methods.

6. The method of claim 1, wherein the three-dimensional cutting surface of the patient-specific broach includes cutting teeth and channels for moving bone chips away from a cavity created by the patient-specific broach.

7. The method of claim 1, further comprising designing the patient-specific broach to include a coupling component for coupling the patient-specific broach to a non-custom driver tool.

8. The method of claim 7, wherein the coupling component includes a first rod extending from a proximal end surface of the patient-specific broach to be received in a first bore defined through a distal end surface of the non-custom driver tool.

9. A method for preparing a femoral neck for receiving a neck implant comprising:
    obtaining image data of a proximal femoral bone and femoral neck of a specific patient by a medical imaging method;
    constructing a three-dimensional image model of the proximal femoral bone and neck of the specific patient using the image data;
    identifying a three-dimensional cortical boundary surface at an interface between cortical and cancellous bone of the specific patient using the three-dimensional image model;
    designing a patient-specific broach having a three-dimensional cutting surface matching as a negative mold the cortical boundary surface of the specific patient using the three-dimensional image model and configured for removing the cancellous bone without removing the cortical bone;
    manufacturing the patient-specific broach; and
    designing the patient-specific broach to include a coupling component for coupling the patient-specific broach to a non-custom driver tool wherein the coupling component includes a second bore defined through a proximal end surface of the patient-specific broach for receiving a second rod extending from a distal end surface of the non-custom driver tool.

10. A method for preparing a femoral neck for receiving a neck implant comprising:
    obtaining image data of a proximal femoral bone and femoral neck of a specific patient by a medical imaging method;
    constructing a three-dimensional image model of the proximal femoral bone and neck of the specific patient using the image data;
    identifying a three-dimensional cortical boundary surface at an interface between cortical and cancellous bone of the specific patient using the three-dimensional image model;
    designing a patient-specific broach having a three-dimensional cutting surface matching as a negative mold the cortical boundary surface of the specific patient using the three-dimensional image model and configured for removing the cancellous bone without removing the cortical bone, the patient-specific broach including a coupling component for coupling the patient-specific broach to a non-custom driver tool, the coupling component including a first rod extending from a proximal end surface of the patient-specific broach to be received in a first bore defined through a distal end surface of the non-custom driver tool, the coupling component including a second bore defined through the proximal end surface of the patient-specific broach for receiving a second rod extending from the distal end surface of the non-custom driver tool; and
    manufacturing the patient-specific broach.

11. The method of claim 10, wherein obtaining image data of a proximal femoral bone and femoral neck of a specific patient includes obtaining the image data using at least one of MRI and ultrasound imaging methods.

12. The method of claim 10, wherein the three-dimensional cutting surface of the patient-specific broach includes cutting teeth and channels for moving bone chips away from a cavity created by the patient-specific broach.

* * * * *